United States Patent [19]

Smithen

[11] 4,241,060
[45] Dec. 23, 1980

[54] NITROIMIDAZOLES AND COMPOSITIONS THEREOF

[75] Inventor: Carey E. Smithen, Welwyn Garden City, England

[73] Assignee: Hoffmann-La Roche Inc., Nutley, N.J.

[21] Appl. No.: 930,622

[22] Filed: Aug. 3, 1978

[30] Foreign Application Priority Data

Aug. 19, 1977 [GB] United Kingdom .............. 34908/77
May 15, 1978 [GB] United Kingdom .............. 19534/78

[51] Int. Cl.$^3$ ................. C07D 413/06; C07D 233/91; A61K 31/535; A61K 31/415
[52] U.S. Cl. ........................... 424/248.57; 424/246; 424/250; 424/267; 544/58.5; 544/139; 544/370; 546/210; 548/336; 548/339; 260/245.5
[58] Field of Search ............... 546/210; 548/336, 338, 548/339; 424/267, 273 R, 246, 248.57, 250; 544/139, 370, 58.5; 260/245.5

[56] References Cited

U.S. PATENT DOCUMENTS

| 3,646,057 | 2/1972 | Beaman et al. ................. 548/338 |
| 4,038,410 | 7/1977 | Rufer et al. .................... 548/336 |

FOREIGN PATENT DOCUMENTS

746007 11/1966 Canada ................................ 548/338

OTHER PUBLICATIONS

Adams et al., "Radiation Research", v. 67, (1976), pp. 9-20.
Chapman et al., "Cancer", v. 40, (1977), pp. 484–488.
Brown et al., "Br. J. Cancer", vol. 37, Suppl. III, 1978, pp. 206–211.
Rauth et al., "British J. Cancer", (1978), 37, Suppl. III, pp. 202–205.
Brown, "British J. Cancer", (1978), 38, Suppl. III, pp. 206–211.

*Primary Examiner*—Henry R. Jiles
*Assistant Examiner*—R. W. Ramsuer
*Attorney, Agent, or Firm*—Jon S. Saxe; George M. Gould; Peter R. Shearer

[57] ABSTRACT

Nitroimidazoles of the formula

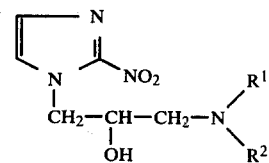

wherein $R^1$ and $R^2$ are as hereinafter set forth, are described. The nitroimidazoles are useful as hypoxic-cell radiosensitizers, as well as being useful as antiprotozoal agents.

20 Claims, No Drawings

NITROIMIDAZOLES AND COMPOSITIONS THEREOF

BRIEF SUMMARY OF THE INVENTION

The invention relates to nitroimidazoles of the formula

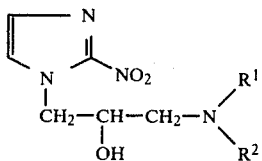

wherein $R^1$ is hydrogen, lower alkyl, hydroxy-(lower alkyl), lower cycloalkyl, aryl or lower aralkyl and $R^2$ is lower alkyl, hydroxy-(lower alkyl), lower cycloalkyl, aryl or lower aralkyl or a grouping of the formula

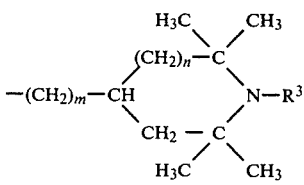

wherein m is zero and n is 1 or m is 1 and n is zero, and $R^3$ is hydrogen, methyl, hydroxy or an oxy free radical, or $R^1$ and $R^2$, when taken together with the nitrogen atom to which they are attached, are a 5-membered, 6-membered or 7-membered saturated heteromonocyclic ring which may carry a hydroxy group on a carbon atom other than a carbon atom attached directly to the nitrogen atom or which may contain an oxygen or sulfur atom or an additional nitrogen which may be substituted by lower alkyl, hydroxy-(lower alkyl), aryl or lower aralkyl, and acid addition salts thereof.

DETAILED DESCRIPTION OF THE INVENTION

The nitroimidazoles of the invention are compounds of the formula

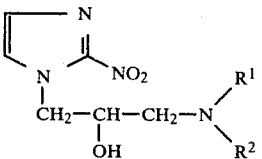

wherein $R^1$ is hydrogen, lower alkyl, hydroxy-(lower alkyl), lower cycloalkyl, aryl or lower aralkyl and $R^2$ is lower alkyl, hydroxy-(lower alkyl), lower cycloalkyl, aryl or lower aralkyl or a grouping of the formula

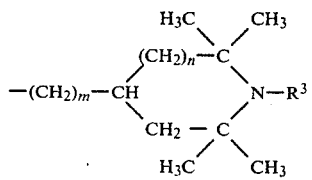

wherein m is zero and n is 1 or m is 1 and n is zero, and $R^3$ is hydrogen, methyl, hydroxy or an oxy free radical, or $R^1$ and $R^2$ together with the nitrogen atom to which they are attached are a 5-membered, 6-membered or 7-membered saturated heteromonocyclic ring which may be substituted by hydroxy on a carbon atom other than a carbon atom attached directly to the nitrogen atom or which may contain an oxygen or sulfur or an additional nitrogen which may be substituted by lower alkyl, hydroxy-(lower alkyl), aryl or lower aralkyl, and acid addition salts thereof.

As used herein, the term "lower alkyl" denotes a straight-chain or branched-chain alkyl group which preferably contains from 1 to 6 carbon atoms, for example, methyl, ethyl, propyl, isopropyl, butyl, tert.-butyl, pentyl, hexyl, and the like. Examples of hydroxy-(lower alkyl) groups are hydroxymethyl, 2-hydroxyethyl, 2-hydroxypropyl, 3-hydroxypropyl, 2-hydroxybutyl, and the like. The term "lower cycloalkyl" denotes a cycloalkyl group which preferably contains 3 to 6 carbon atoms, for example, cyclopropyl, cyclopentyl and cyclohexyl. The term "aryl" denotes phenyl or a phenyl group carrying one or more, preferably one or two, substituents selected from halogen, for example, fluorine, chlorine, bromine or iodine, trifluoromethyl, lower alkyl, lower alkoxy, nitro, amino and the like. Examples of substituted-phenyl groups are 4-chlorophenyl, 2,4-dichlorophenyl, p-tolyl, 4-methoxyphenyl, 4-nitrophenyl, 4-aminophenyl and the like. The term "lower aralkyl" denotes a lower alkyl group in which one of the hydrogen atoms has been replaced by an aryl group as hereinbefore described. Examples of lower aralkyl groups are benzyl, 4-chlorobenzyl, phenethyl, phenylpropyl and the like. Examples of saturated heteromonocyclic rings which are formed by $R^1$ and $R^2$ and the nitrogen atom to which they are attached and which may carry a hydroxy group on a carbon atom other than a carbon atom attached directly to the nitrogen atom are pyrrolidino, piperidino, 3-hydroxypyrrolidino, 4-hydroxy-piperidino, 3-hydroxy-hexahydro-1H-azepino and the like. Examples of saturated heteromonocyclic rings which are formed by $R^1$ and $R^2$ and the nitrogen atom to which they are attached and which contain an oxygen or sulfur atom or an additional nitrogen atom which may be substituted as described earlier are piperazino, N-methylpiperazino, N-(2-hydroxyethyl)piperazino, morpholino, thiamorpholino and the like. The term "lower alkoxy" denotes a straight-chain or branched-chain alkoxy group which preferably contains from 1 to 6 carbon atoms, for example, methoxy, ethoxy, and the like.

A preferred group of nitroimidazole derivatives of the invention comprises compounds of formula I wherein $R^1$ is hydrogen, lower alkyl, hydroxy-(lower alkyl), aryl or lower aralkyl and $R^2$ is lower alkyl, hydroxy-(lower alkyl), aryl or lower aralkyl or $R^1$ and $R^2$ taken together with the nitrogen atom to which they are attached are a 5-membered, 6-membered or 7-membered saturated heteromonocyclic ring which may contain an oxygen or sulfur atom or an additional nitrogen atom which may be substituted by lower alkyl, hydroxy-(lower alkyl), aryl or lower aralkyl, and pharmaceutically acceptable acid addition salts thereof.

An especially preferred group of nitroimidazole derivatives of the invention comprises compounds of formula I wherein $R^1$ and $R^2$ taken together with the nitrogen atom to which they are attached are a 6-membered heteromonocyclic ring which may contain an oxygen or an additional nitrogen which may be substituted by lower alkyl, and pharmaceutically acceptable acid addition salts thereof.

Exemplary of compounds of formula I hereinbefore are:

2-nitro-α-(piperidino)methyl-1-imidazole-ethanol,
α-(morpholino)methyl-2-nitro-1-imidazole-ethanol,
α-(4-methylpiperazino)methyl-2-nitro-1-imidazole-ethanol,
2-nitro-α-(pyrrolidino)methyl-1-imidazole-ethanol,
α-(diethylamino)methyl-2-nitro-1-imidazole-ethanol,
α-[di(2-hydroxyethyl)amino]methyl-2-nitro-1-imidazole-ethanol,
α-(tert.-butylamino)methyl-2-nitro-1-imidazole-ethanol,
α-(benzylamino)methyl-2-nitro-1-imidazole-ethanol,
α-[(4-methoxyphenyl)amino]methyl-2-nitro-1-imidazole-ethanol,
α-(dimethylamino)methyl-2-nitro-1-imidazole-ethanol,
α-(hexahydro-1H-azepino)methyl-2-nitro-1-imidazole-ethanol,
4-[2-hydroxy-3-(2-nitro-1-imidazolyl)propylamino]-2,2,6,6-tetramethylpiperidin-N-oxy,
α-[(2,2,6,6-tetramethyl-4-piperidinyl)amino]methyl-2-nitro-1-imidazole-ethanol,
α-(cyclohexylamino)methyl-2-nitro-1-imidazole-ethanol,
α-(dicyclohexylamino)methyl-2-nitro-1-imidazole-ethanol, and
1-[2-hydroxy-3-(2-nitro-1-imidazolyl)propyl]-3-pyrrolidinol.

In accordance with the process of the present invention, the nitroimidazole derivatives, that is, the compounds of formula I and their acid addition salts, are prepared by (a) reacting the epoxide of the formula

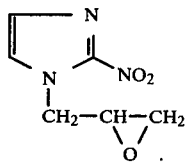

II with an amine of the formula

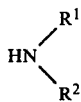

III wherein $R^1$ and $R^2$ are as previously described, or (b) to prepare a compound of formula I wherein $R^1$ is other than hydrogen, condensing the compound of the formula

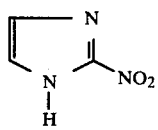

IV with an epoxide of the formula

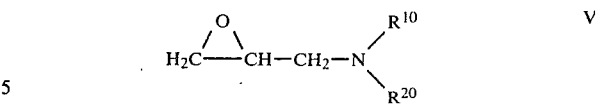

V wherein $R^{10}$ and $R^{20}$ are the same as $R^1$ and $R^2$ hereinbefore, except that $R^{10}$ is not hydrogen, in the presence of a base, or (c) reacting a halohydrin of the formula

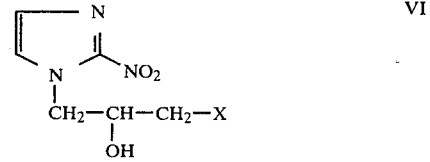

VI wherein X is chlorine or bromine, with an amine of formula III hereinbefore, and, if desired, converting an obtained compound of formula I into an acid addition salt, particularly pharmaceutically acceptable acid addition salts.

The reaction of the epoxide of formula II with an amine of formula III in accordance with process embodiment (a) can be carried out in the presence or absence of an inert organic solvent. When an inert organic solvent is used, this may suitably be a lower alkanol, for example, methanol, ethanol, or the like, dimethylformamide, dimethylacetamide or the like. Alternatively, an excess of an amine of formula III can be used and can thereby serve as the solvent. The temperature and pressure at which the reaction is carried out are not critical. Thus, the reaction may be carried out at room temperature and atmospheric pressure or at an elevated temperature and/or pressure. In a preferred procedure, the reaction is carried out at a temperature in the range of from about 50° C. up to the reflux temperature of the reaction mixture and at atmospheric pressure.

The condensation of the compound of formula IV, which is azomycin, with an epoxide of formula V in accordance with process embodiment (b) is carried out in the presence of a base. The base is preferably used in catalytic amounts, although larger amounts of base can be used, if desired. Preferred bases are alkali metal carbonates, for example, sodium carbonate, potassium carbonate or the like, although other bases such as alkali metal hydroxides, for example, sodium hydroxide, potassium hydroxide, or the like, can also be used. The condensation is conveniently carried out in the presence of an inert organic solvent which may suitably be a lower alkanol, for example, methanol, ethanol or the like. Although the condensation can be carried out at room temperature and atmospheric pressure or at an elevated temperature and/or pressure, it is preferably carried out at an elevated temperature, especially at the reflux temperature of the condensation mixture, and at atmospheric pressure.

The reaction of a halohydrin of formula VI hereinbefore with an amine of formula III hereinbefore in accordance with process embodiment (c) is conveniently carried out using at least one mol of amine per mol of halohydrin. The reaction is conveniently carried out in the presence of an acid-binding agent, for example, an alkali metal carbonate, such as, sodium carbonate, potassium carbonate, or the like, or a tertiary organic amine, such as, pyridine or, preferably, an excess of the amine of formula III. Accordingly, it is especially preferred to carry out the reaction using at least two moles of amine of formula III for each mol of halohydrin of formula VI. The reaction is conveniently carried out in the presence of an inert organic solvent which may suitably be a lower alkanol, such as, methanol, ethanol, or the like. The temperature and pressure at which the reaction is carried out are not critical. It may be carried out at room temperature and atmospheric pressure or at an elevated temperature and/or pressure. In a preferred procedure, the reaction is carried out at an elevated temperature, especially at the reflux temperature of the reaction mixture, and at atmospheric pressure. The preferred halohydrin of formula VI hereinbefore is the chlorohydrin.

The compounds of formula I can be converted into acid addition salts by treatment with an inorganic acid, for example, a hydrohalic acid, such as, hydrochloric acid or hydrobromic acid, sulfuric acid, nitric acid, phosphoric acid, or the like, or with an organic acid, such as, acetic acid, citric acid, maleic acid, malic acid, fumaric acid, succinic acid, methanesulfonic acid, para-toluenesulfonic acid, or the like. The pharmaceutically acceptable acid addition salts, especially the hydrochlorides, are preferred. Non-pharmaceutically acceptable acid addition salts can be converted into pharmaceutically acceptable acid addition salts by treatment with a base to form a compound of formula I and treatment of said compound with a pharmaceutically accetpable acid.

The starting materials used in the foregoing processes, namely, the epoxide of formula II, the amines of formula III, the compound of formula IV, the epoxides of formula V and the halohydrins of formula VI, are known compounds.

The compounds of formula I and their pharmaceutically acceptable acid addition salts are useful in sensitizing hypoxic cells to the effects of radiation. Accordingly, they may be used as hypoxic-cell radiosensitizers in conjunction with the treatment of hypoxic tumor cells with radiation. The effectiveness of compounds of formula I and pharmaceutically acceptable acid addition salts thereof as hypoxic-cell radiosensitizers can be demonstrated in vitro using hypoxic Chinese hamster V79 cells (see Adams et al., Radiation Research, 1976, 67, 9-20). For example, 2-nitro-α-(piperidino)methyl-1-imidazole-ethanol hydrochloride and α-(benzylamino)-methyl-2-nitro-1-imidazole-ethanol hydrochloride, two nitroimidazole derivatives of the invention, provide an enhancement ratio of 1.6 ($ER_{1.6}$) at concentrations of 30 micromoles and 40 micromoles, respectively. In order to achieve the same enhancement ratio with misonidazole and metronidazole, both of which are known nitroimidazoles, a concentration thereof of 300 micromoles and 4000 micromoles, respectively, is required.

The compounds of formula I and their pharmaceutically acceptable acid addition salts are also useful in combatting protozoal infections, especially infections caused by Trichomonas vaginalis. Accordingly, they may be used as antiprotozoal agents.

The compounds of formula I and their pharmaceutically acceptable acid addition salts can be used as medicaments in the form of pharmaceutical preparations which contain them in association with a compatible pharmaceutical carrier material. The carrier material can be an organic or inorganic inert carrier material which is suitable for enteral, for example, oral or parenteral administration; for example, water, gelatin, lactose, starch, magnesium stearate, talc, vegetable oils, gum arabic, polyalkyleneglycols, and the like. The pharmaceutical preparations may be made up in solid form, for example, as tablets, dragees, suppositories or capsules, or in liquid form, for example, as solutions, suspensions or emulsions. The pharmaceutical preparations may be sterilized and/or may contain adjuvants, such as, preserving, stabilizing, wetting or emulsifying agents, salts for varying the osmotic pressure or buffers. The pharmaceutical preparations may also contain other therapeutically valuable substances.

When used for the sensitization of hypoxic tumor cells in conjunction with single or multiple dose radiotherapy regimens, the compounds of formula I and their pharmaceutically acceptable acid addition salts can be administered orally in a daily dosage of from about 20 mg/kg body weight to about 60 mg/kg body weight. In general, the total dosage should not exceed about 200 mg/kg body weight for any one course of multiple-dose treatment. When used as antiprotozoal agents, the compounds of formula I and their pharmaceutically acceptable acid addition salts can be administered orally in a daily dosage of from about 20 mg/kg body weight to about 60 mg/kg body weight. It will be appreciated that the aforementioned dosage ranges are given by way of example only and that they can be increased or decreased depending on individual requirements.

The pharmaceutical preparations are prepared in accordance with known procedures. More specifically, the active ingredient, that is, a compound of formula I or a pharmaceutically acceptable acid addition salt thereof, is mixed with non-toxic, inert, therapeutically compatible solid or liquid carriers, commonly used in such preparations and is formulated into a suitable pharmaceutical dosage form.

The Examples which follow further illustrate the invention. All temperatures are in degrees Centigrade, unless otherwise mentioned.

EXAMPLE 1

(al) A mixture of 5.1 g (30 mmol) of 1-(2,3-epoxypropyl)-2-nitroimidazole, 3.3 g (45 mmol) of diethylamine and 100 ml of methanol was heated under reflux for 12–18 hours. The solvent was removed under reduced pressure to give 8.1 g of a pale brown residue which was redissolved in ca. 25 ml of hot ethanol, treated with decolorizing charcoal, filtered and allowed to crystallize to give 5.2 g (72% yield) of α-(diethylamino)methyl-2-nitro-1-imidazole-ethanol as a pale yellow crystalline solid of melting point 92°–93° C.

(b) 3.6 g of α-(diethylamino)methyl-2-nitro-1-imidazole-ethanol were dissolved in a minimum amount of warm ethanol and treated with a small excess of anhydrous ethereal hydrogen chloride. The mixture was then allowed to cool and crystallize for several hours. There were obtained 4.0 g of cream colored hydrochloride salt. This was collected, redissolved in ca. 40 ml of hot ethanol, treated with decolorizing charcoal, filtered and allowed to crystallize after the addition of a few ml of anhydrous diethyl ether if necessary, to yield 4.0 g of α-(diethylamino)methyl-2-nitro-1-imidazole-ethanol hydrochloride in the form of a very pale cream colored microcrystalline solid of melting point 145°–146° C. (decomposition).

EXAMPLE 2

(a) In a manner analogous to that described in Example 1(a) there was obtained, after crystallization from isopropanol, 2-nitro-α-(pyrrolidino)methyl-1-imidazole-ethanol in the form of a pale yellow crystalline solid of melting point 83°–85° C.; yield 79%.

(b) In a manner analogous to that described in Example 1(b) there was obtained 2-nitro-α-(pyrrolidino)methyl-1-imidazole-ethanol hydrochloride in the form of a very pale cream colored microcrystalline solid of melting point 158°–159° C. (decomposition); yield 87%.

EXAMPLE 3

(a) In a manner analogous to that described in Example 1(a) there was obtained, after crystallization from ethanol, 2-nitro-α-(piperidino)methyl-1-imidazole-ethanol in the form of a pale yellow crystalline solid of melting point 110°–112° C.; yield 88%.

(b) In a manner analogous to that described in Example 1(b) there was obtained 2-nitro-α-(piperidino)methyl-1-imidazole-ethanol hydrochloride in the form of a very pale cream colored microcrystalline solid of melting point 144°–145° C. (decomposition); yield 90%.

EXAMPLE 4

(a) In a manner analogous to that described in Example 1(a) there was obtained, after crystallization from ethanol, α-(morpholino)methyl-2-nitro-1-imidazole-ethanol in the form of a pale yellow crystalline solid of melting point 112°–113° C.; yield 88%.

(b) In a manner analogous to that described in Example 1(b) there was obtained α-(morpholinomethyl)-2-nitro-1-imidazole-ethanol hydrochloride in the form of a very pale cream colored microcrystalline solid of melting point 196°–197° C. (decomposition); yield 93%.

EXAMPLE 5

(a) In a manner analogous to that described in Example 1(a) there was obtained, after crystallization from ethanol, α-(4-methylpiperazino)methyl-2-nitro-1-imidazole-ethanol in the form of a pale yellow crystalline solid of melting point 144°–145° C.; yield 62%.

(b) In a manner analogous to that described in Example 1(b) there was obtained α-(4-methylpiperazino)-methyl-2-nitro-1-imidazole-ethanol dihydrochloride in the form of an almost colorless microcrystalline solid of melting point 215°–216° C. (decomposition); yield 77%.

EXAMPLE 6

(a) In a manner analogous to that described in Example 1(a), but using equimolar amounts of reagents, there was obtained, after crystallization from isopropanol, α-[di-(2-hydroxyethyl)amino]methyl-2-nitro-1-imidazole-ethanol in the form of a pale yellow crystalline solid of melting point 92°–93° C.; yield 79%.

(b) In a manner analogous to that described in Example 1(b) there was obtained α-[di-(2-hydroxyethyl)amino]methyl-2-nitro-1-imidazole-ethanol hydrochloride in the form of a very pale cream colored microcrystalline solid of melting point 151°–152° C. (decomposition); yield 75%.

EXAMPLE 7

(a) In a manner analogous to that described in Example 1(a), but using two molar equivalents of tert.-butylamine, there was obtained, after crystallization from ethanol α-(tert.-butylamino)methyl-2-nitro-1-imidazole-ethanol in the form of a pale yellow crystalline solid of melting point 114°–115° C.; yield 36%.

(b) In a manner analogous to that described in Example 1(b) there was obtained α-(tert.-butylamino)methyl-2-nitro-1-imidazole-ethanol hydrochloride in the form of a very pale cream colored microcrystalline solid of melting point 198°–199° C. (decomposition); yield 87%.

EXAMPLE 8

(a) In a manner analogous to that described in Example 1(a), but using equimolar amounts of reagents, there was obtained α-(benzylamino)methyl-2-nitro-1-imidazole-ethanol in the form of a pale yellow gum which was homogeneous according to thin-layer chromatography.

(b) 4.5 g of α-(benzylamino)methyl-2-nitro-1-imidazole-ethanol were dissolved in a minimum amount of warm ethanol and treated with an equivalent amount of ethanolic maleic acid (1.9 g). The mixture was allowed to cool and crystallize for several hours. There were obtained 5.2 g of cream colored hydrogen maleate salt. This was collected, redissolved in ca. 50 ml of hot ethanol, treated with decolorizing charcoal, filtered and allowed to crystallize, after addition of a few ml of anhydrous diethyl ether if necessary, to yield 3.6 g of α-(benzylamino)methyl-2-nitro-1-imidazole-ethanol hydrogen maleate in the form of a very pale cream colored microcrystalline solid of melting point 153°–154° C. (decomposition).

(c) In a manner analogous to that described in part (b) of this Example there was obtained, after crystallization from ethanol, α-(benzylamino)methyl-2-nitro-1-imidazole-ethanol hydrogen oxalate in the form of a colorless microcrystalline solid of melting point 197°–198° C. (decomposition).

EXAMPLE 9

(a) In a manner analogous to that described in Example 1(a), but using equimolar amounts of reagents, there was obtained, after crystallization from ethanol, α-[(4-methoxyphenyl)amino]methyl-2-nitro-1-imidazole-ethanol in the form of a brown crystalline solid (needles) of melting point 162°–163° C.; yield 80%.

(b) In a manner analogous to that described in Example 1(b) there was obtained α-[(4-methoxyphenyl)amino]methyl-2-nitro-1-imidazole-ethanol hydrochloride in the form of a very pale pink colored microcrystalline solid of melting point 156°–157° C. (decomposition); yield 97%.

EXAMPLE 10

(a) In a manner analogous to that described in Example 1(a) there was obtained, after recrystallization from isopropanol, α-(dimethylamino)methyl-2-nitro-1-imidazole-ethanol in the form of a pale yellow crystalline solid of melting point 78°–79° C.; yield 40%.

(b) In a manner analogous to that described in Example 1(b) there was obtained, after recrystallization from methanol/diethyl ether, α-(dimethylamino)methyl-2-nitro-1-imidazole-ethanol hydrochloride in the form of a colorless microcrystalline solid of melting point 202°–203° C. (decomposition).

EXAMPLE 11

(a) In a manner analogous to that described in Example 1(a) there was obtained, after recrystallization from isopropanol, α-(hexahydro-1H-azepino)methyl-2-nitro-1-imidazole-ethanol in the form of a pale yellow crystalline solid of melting point 102°–103° C.

(b) In a manner analogous to that described in Example 1(b) there was obtained, after recrystallization from ethanol/diethyl ether, α-(hexahydro-1H-azepino)methyl-2-nitro-1-imidazole-ethanol hydrochloride in the form of an almost colorless crystalline solid of melting point 133°–134° C. (decomposition).

EXAMPLE 12

In a manner analogous to that described in Example 1(a) there was obtained from 4-amino-2,2,6,6-tetramethylpiperidin-N-oxyl in 62% yield, after chromatography on alumina (elution being carried out with dichloromethane, the eluates of the red-orange band being combined and concentrated and the concentrate being left to crystallize), 4-[2-hydroxy-3-(2-nitro-1-imidazolyl)propylamino]-2,2,6,6-tetramethylpiperidin-N-oxyl in the form of an orange colored crystalline solid of melting point 150°–151° C.

EXAMPLE 13

In a manner analogous to that described in Example 1(a) there was obtained, after recrystallization from isopropanol, α-[(2,2,6,6-tetramethyl-4-piperidinyl)amino]methyl-2-nitro-1-imidazole-ethanol in the form of a cream colored solid of melting point 151°–153° C.; yield 60%.

EXAMPLE 14

(a) In a manner analogous to that described in Example 1(a) there was obtained, after recrystallization from isopropanol, α-(cyclohexylamino)methyl-2-nitro-1-imidazole-ethanol in the form of a cream colored crystalline solid of melting point 66°–68° C.; yield 90%.

(b) In a manner analogous to that described in Example 1(b) there was obtained, after recrystallization from ethanol/diethyl ether, α-(cyclohexylamino)methyl-2-nitro-1-imidazole-ethanol hydrochloride in the form of an almost colorless microcrystalline solid of melting point 192°–193° C. (decomposition).

EXAMPLE 15

(a) In a manner analogous to that described in Example 1(a) there was obtained, after recrystallization from ethanol, α-(dicyclohexylamino)methyl-2-nitro-1-imidazole-ethanol in the form of a yellow-orange crystalline solid of melting point 149°–150° C.; yield 31%.

(b) In a manner analogous to that described in Example 1(b) there was obtained, after recrystallization from ethanol/diethyl ether, α-(dicyclohexylamino)methyl-2-nitro-1-imidazole-ethanol hydrochloride in the form of a cream colored microcrystalline solid of melting point 208°–209° C. (decomposition).

EXAMPLE 16

In a manner analogous to that described in Example 1(a) there was obtained, after recrystallization from ethanol, 1-[2-hydroxy-3-(2-nitro-1-imidazolyl)propyl]-3-pyrrolidinol in the form of a cream colored crystalline solid of melting point 126°–130° C.

EXAMPLE 17

(a) A mixture of 5.65 g (50 mmol) of 2-nitroimidazole and 250 mg of anhydrous potassium carbonate in 150 ml of ethanol was heated under reflux for 15 minutes. 7.05 g (50 mmol) of freshly distilled 3-piperidino-propylene oxide in a minimum amount of ethanol were added to the mixture and heating under reflux was continued for 3 hours. The mixture was filtered and the filtrate was evaporated to dryness in vacuo to give ca. 13 g of a yellow oil which was partitioned between 100 ml of ethyl acetate and 100 ml of water. The aqueous layer was separated and washed once with 50 ml of ethyl acetate. The combined organic phases were extracted with four 50 ml portions of 2-N hydrochloric acid. The combined aqueous-acidic solutions were made basic by the addition of excess solid sodium carbonate and extracted with three 100 ml portions of dichloromethane. The combined organic phases were dried over anhydrous sodium carbonate and filtered. The filtrate was evaporated to dryness in vacuo to give 6.5 g of a pale yellow solid which was redissolved in 25 ml of hot ethanol, treated with decolorizing charcoal, filtered and left to crystallize, there being obtained 1.4 g (11% yield) of 2-nitro-α-(piperidino)methyl-1-imidazole-ethanol in the form of a pale yellow crystalline solid of melting point 108°–109° C.

(b) 1.27 g of 2-nitro-α-(piperidino)methyl-1-imidazole-ethanol were dissolved in 25 ml of warm ethanol and treated with a small excess of anhydrous ethereal hydrogen chloride. The mixture was then allowed to cool and crystallize for several hours. There were obtained 1.4 g of 2-nitro-α-(piperidino)methyl-1-imidazole-ethanol hydrochloride in the form of a very pale cream colored microcrystalline solid identical with the product prepared as described in Example 3(b).

EXAMPLE 18

A mixture of 4.1 g (20 mmol) of 3-chloro-1-(2-nitro-1-imidazolyl)-2-propanol, 3.4 g (40 mmol) of piperidine and 75 ml of methanol was heated under reflux for 12–18 hours. The solvent was removed under reduced pressure to give 7.3 g of a cream colored solid which was suspended in 75 ml of water and acidified with a small excess of 2-N hydrochloric acid. The homogeneous solution was washed with three 25 ml portions of dichloromethane and the dichloromethane washings were discarded. The aqueous solution was treated with a small excess of 2-N sodium hydroxide solution and extracted with three 75 ml portions of fresh dichloromethane. The dichloromethane extracts were combined, dried over anhydrous magnesium sulfate, filtered and evaporated to dryness in vacuo to give 4.3 g of a cream colored solid. This solid was dissolved in ca. 25 ml of hot ethanol, treated with decolorizing charcoal, filtered and allowed to crystallize to give 3.3 g (65% yield) of 2-nitro-α-(piperidino)methyl-1-imidazole-ethanol in the form of a pale yellow crystalline solid of melting point 110°–112° C. This product was identical with the product prepared as described in Example 3(a) and was converted into the hydrochloride in a manner analogous to that described in Example 1(b).

The following Example illustrates a typical pharmaceutical preparation containing a compound of formula I or a pharmaceutically acceptable acid addition salt thereof (hereinafter referred to as the "active ingredient"):

EXAMPLE A

| Capsule formulation: | Per capsule |
|---|---|
| Active ingredient | 500.00 mg |
| Cellulose | 10.00 mg |
| Methylhydroxypropylcellulose | 5.00 mg |
| Dioctyl sodium sulfosuccinate | 1.00 mg |
| Maize starch | 12.00 mg |
| Magnesium stearate | 2.00 mg |
| Total weight | 530.00 mg |

I claim:

1. A compound of the formula

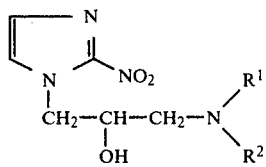

wherein $R^1$ is hydrogen, lower alkyl, hydroxy-(lower alkyl), lower cycloalkyl, aryl or lower aralkyl and $R^2$ is lower alkyl, hydroxy-(lower alkyl), lower cycloalkyl, aryl or lower aralkyl or a grouping of the formula

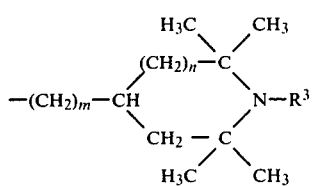

wherein m is zero and n is 1 or m is 1 and n is zero and $R^3$ is hydrogen, methyl or hydroxy, or $R^1$ and $R^2$ taken together with the nitrogen atom to which they are attached are a 5-membered, 6-membered or 7-membered saturated heteromonocyclic ring selected from pyrrolidino, piperidino, 3-hydroxypyrrolidino, 4-hydroxypiperidino, 3-hydroxy-hexahydro-1H-azepino, piperazino, . N-methylpiperazino, N-(2-hydroxyethyl)piperazino, morpholino, hexahydro-1H-azepino, and thiamorpholino, or an acid addition salt thereof.

2. A compound in accordance with claim 1, wherein $R^1$ is hydrogen, lower alkyl, hydroxy-(lower alkyl), aryl or lower aralkyl and $R^2$ is lower alkyl, hydroxy-(lower alkyl), aryl or lower aralkyl or $R^1$ and $R^2$ taken together with the nitrogen atom to which they are attached are a 5-membered, 6-membered or 7-membered saturated heteromonocyclic ring selected from pyrrolidino, piperidino, piperazino, N-methylpiperazino, N-(2-hydroxyethyl)piperazino, morpholino, hexahydro-1H-azepino and thiamorpholino, or an acid addition salt thereof.

3. A compound in accordance with claim 1, wherein $R^1$ and $R^2$ taken together with the nitrogen atom to which they are attached are a 6-membered heteromonocyclic ring selected from piperidino, piperazino, N-methylpiperazino, morpholino and thiamorpholino, or an acid addition salt thereof.

4. A compound in accordance with claim 1, 2-nitro-α-(piperidino)methyl-1-imidazole-ethanol.

5. A compound in accordance with claim 1, α-(morpholino)methyl-2-nitro-1-imidazole-ethanol.

6. A compound in accordance with claim 1, α-(4-methylpiperazino)methyl-2-nitro-1-imidazole-ethanol.

7. A compound in accordance with claim 1, 2-nitro-α-(pyrrolidino)methyl-1-imidazole-ethanol.

8. A compound in accordance with claim 1, α-(diethylamino)methyl-2-nitro-1-imidazole-ethanol.

9. A compound in accordance with claim 1, α-[di-(2-hydroxyethyl)amino]-methyl-2-nitro-1-imidazole-ethanol.

10. A compound in accordance with claim 1, α-(tert.-butylamino)methyl-2-nitro-1-imidazole-ethanol.

11. A compound in accordance with claim 1, α-(benzylamino)methyl-2-nitro-1-imidazole-ethanol.

12. A compound in accordance with claim 1, α-[(4-methoxyphenyl)amino]methyl-2-nitro-1-imidazole-ethanol.

13. A compound in accordance with claim 1, α-(dimethylamino)methyl-2-nitro-1-imidazole-ethanol.

14. A compound in accordance with claim 1, α-(hexahydro-1H-azepino)methyl-2-nitro-1-imidazole-ethanol.

15. A compound in accordance with claim 1, 4-[2-hydroxy-3-(2-nitro-1-imidazolyl)propylamino]-2,2,6,6-tetramethylpiperidin-N-oxy.

16. A compound in accordance with claim 1, α-[(2,2,6,6-tetramethyl-4-piperidinyl)amino]methyl-2-nitro-1-imidazole-ethanol.

17. A compound in accordance with claim 1, α-(cyclohexylamino)methyl-2-nitro-1-imidazole-ethanol.

18. A compound in accordance with claim 1, α-(dicyclohexylamino)methyl-2-nitro-1-imidazole-ethanol.

19. A compound in accordance with claim 1, 1-[2-hydroxy-3-(2-nitro-1-imidazolyl)propyl]-3-pyrrolidinol.

20. A hypoxic cell radiosensitizing or antiprotozoal pharmaceutical preparation containing a hypoxic cell radiosensitizing amount or an antiprotozoal amount of a compound of the formula

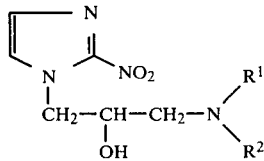

wherein $R^1$ is hydrogen, lower alkyl, hydroxy-(lower alkyl), lower cycloalkyl, aryl or lower aralkyl and $R^2$ is lower alkyl, hydroxy-(lower alkyl), lower cycloalkyl, aryl or lower aralkyl or a grouping of the formula

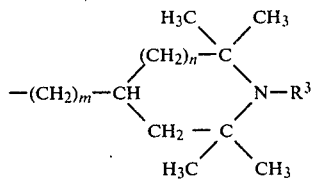

wherein m is zero and n is 1 or m is 1 and n is zero, and $R^3$ is hydrogen, methyl or hydroxy, or $R^1$ and $R^2$ when taken together with the nitrogen atom to which they are attached are a 5-membered, 6-membered or 7-membered saturated heteromonocyclic ring selected from pyrrolidino, piperidino, 3-hydroxypyrrolidino, 4-hydroxypiperidino, 3-hydroxy-1H-azepino, piperazino, N-methylpiperazino, N-(2-hydroxyethyl)piperazino, morpholino, hexahydro-1H-azepino, and thiamorpholino, or a pharmaceutically acceptable acid addition salt thereof, in association with a compatible pharmaceutical carrier material.

* * * * *